US009461421B2

(12) United States Patent
Ogle et al.

(10) Patent No.: US 9,461,421 B2
(45) Date of Patent: Oct. 4, 2016

(54) CATHETER HANDLE

(75) Inventors: David Ogle, Cowan (AU); Gregory James Rogers, Bangor (AU)

(73) Assignee: CathRX LTD, Homebush Bay, NSW (AU)

( * ) Notice: Subject to any disclaimer, the term of this patent is extended or adjusted under 35 U.S.C. 154(b) by 736 days.

(21) Appl. No.: 13/511,441

(22) PCT Filed: Aug. 6, 2010
(Under 37 CFR 1.47)

(86) PCT No.: PCT/AU2010/000999
§ 371 (c)(1),
(2), (4) Date: May 23, 2012

(87) PCT Pub. No.: WO2011/063444
PCT Pub. Date: Jun. 3, 2011

(65) Prior Publication Data
US 2012/0310238 A1    Dec. 6, 2012

Related U.S. Application Data

(60) Provisional application No. 61/265,053, filed on Nov. 30, 2009.

(51) Int. Cl.
| | | |
|---|---|---|
| *H01R 24/58* | (2011.01) |
| *A61M 25/00* | (2006.01) |
| *H01R 12/72* | (2011.01) |
| *H01R 107/00* | (2006.01) |

(52) U.S. Cl.
CPC .......... *H01R 24/58* (2013.01); *A61M 25/0097* (2013.01); *H01R 12/728* (2013.01); *H01R 2107/00* (2013.01); *H01R 2201/12* (2013.01)

(58) Field of Classification Search
CPC .......................... A61M 25/0097; A61B 18/24
USPC .......................................................... 606/41
See application file for complete search history.

(56) References Cited

U.S. PATENT DOCUMENTS

| | | |
|---|---|---|
| 6,024,739 A | 2/2000 | Ponzi et al. |
| 8,641,697 B2 | 2/2014 | Partlett et al. |
| 2007/0005001 A1* | 1/2007 | Rowe et al. ............. 604/19 |
| 2007/0078455 A1 | 4/2007 | Rashidi |

FOREIGN PATENT DOCUMENTS

| | | |
|---|---|---|
| WO | WO01/36017 | 5/2001 |
| WO | WO01/37723 | 5/2001 |
| WO | WO/02/32497 | 4/2002 |
| WO | WO2006/012671 | 9/2006 |

OTHER PUBLICATIONS

International Search Report for PCT/AU2010/000999, dated Oct. 18, 2010.
Written Opinion for PCT/AU2010/000999, dated Oct. 18, 2010.
International Preliminary Report on Patentability for International Application No. PCT/AU2010/000999, dated Jun. 5, 2012, 7 pages.

* cited by examiner

*Primary Examiner* — Joseph Dietrich
(74) *Attorney, Agent, or Firm* — TraskBritt

(57) ABSTRACT

A catheter assembly includes a catheter handle having a handle body defining a bore and having a proximal part and a distal end. A catheter sheath has a proximal part received in the bore of the handle body, the catheter sheath projecting from the distal end of the catheter handle and the proximal part of the catheter sheath carrying a series of spaced electrically conductive members. Each conductive member is electrically connected to a conductor extending in the catheter sheath from the proximal part towards a distal end of the catheter sheath. A carrier is arranged in the bore of the catheter handle, the carrier carrying a series of spaced electrical contacts with each contact being configured to make electrical contact with one of the electrically conductive members of the catheter sheath.

17 Claims, 5 Drawing Sheets

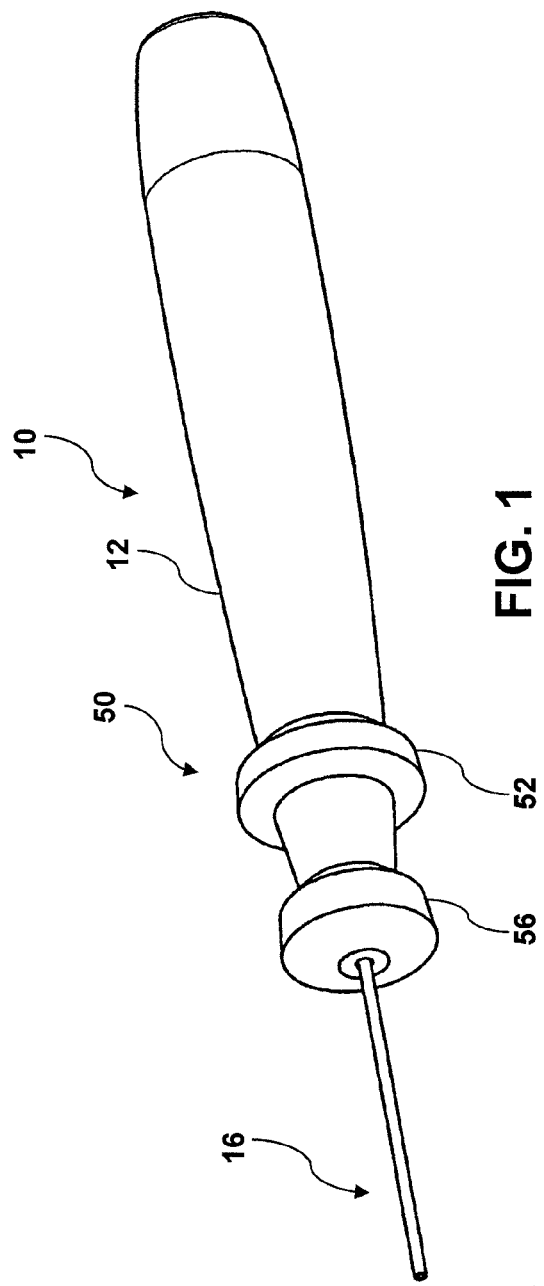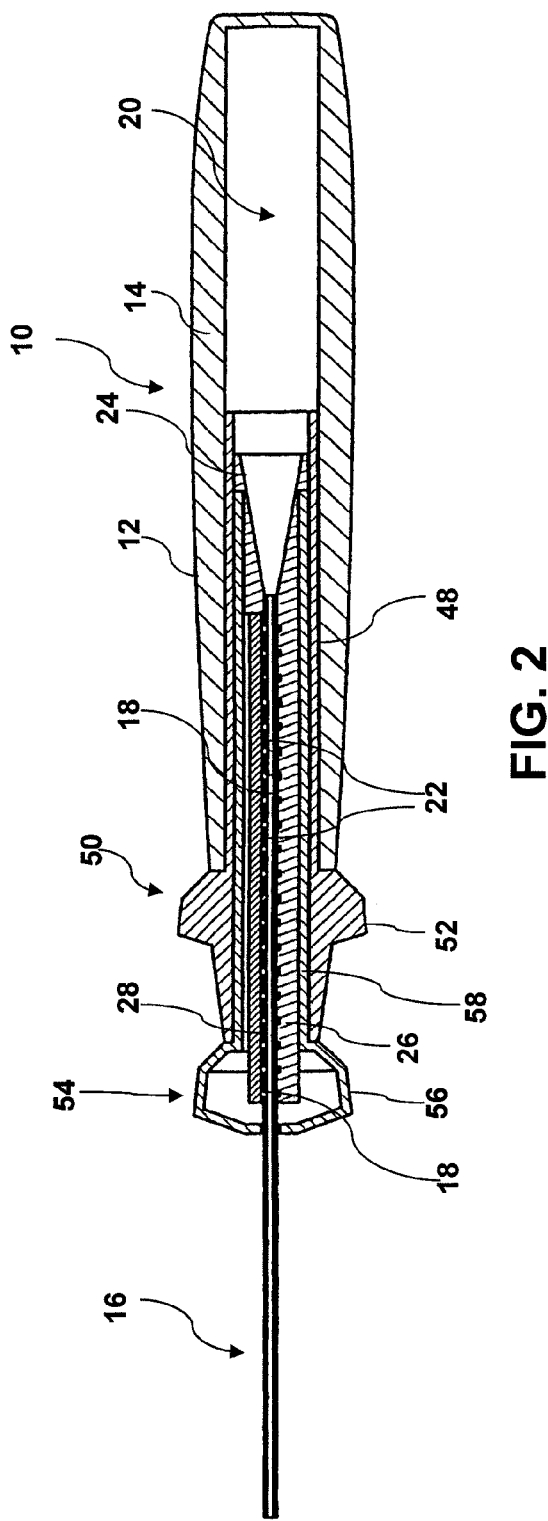

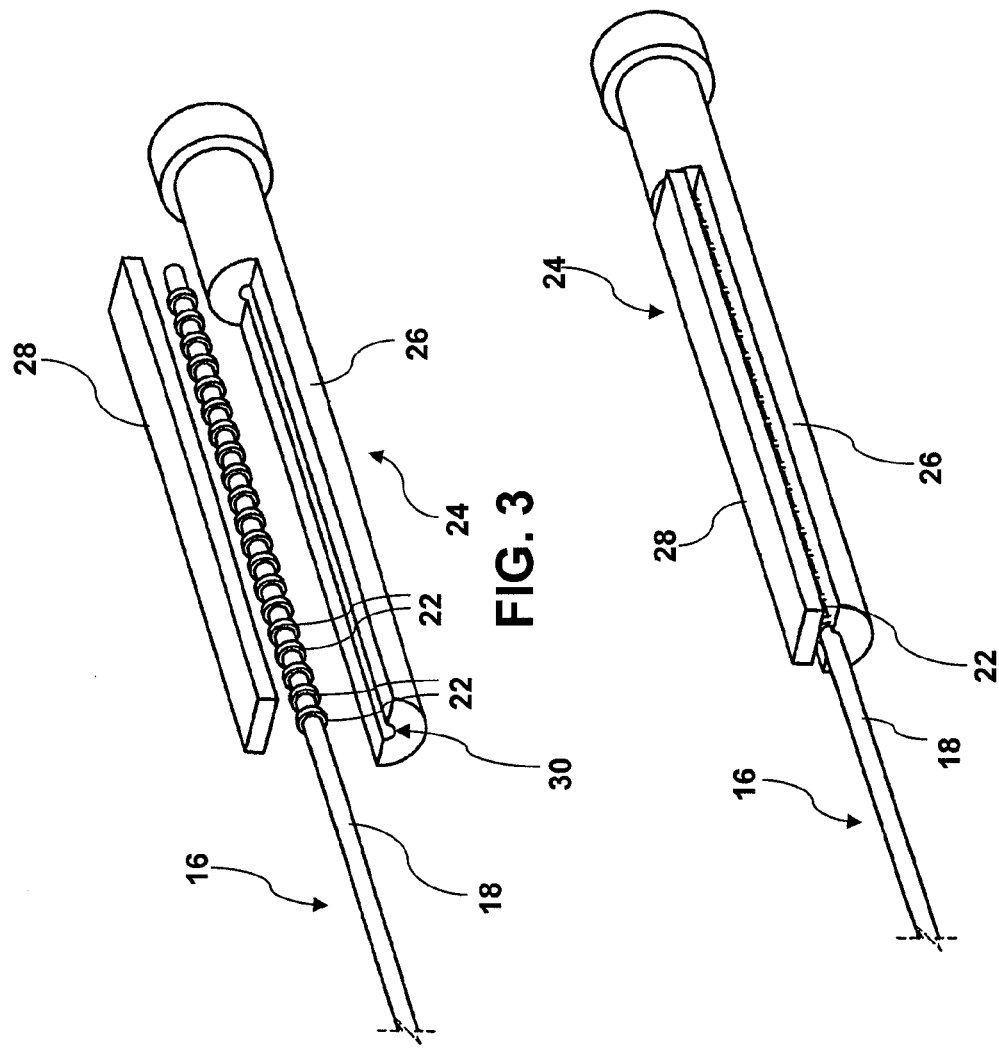

CATHETER HANDLE

CROSS-REFERENCE TO RELATED APPLICATIONS

This is a national phase entry under 35 U.S.C. §371 of International Patent Application PCT/AU2010/000999, filed Aug. 6, 2010, published in English as International Patent Publication WO 2011/063444 A1 on Jun. 3, 2011, which claims the benefit under Article 8 of the Patent Cooperation Treaty of United States Provisional Patent Application Ser. No. 61/265,053, filed Nov. 30, 2009, the entire disclosures of which are hereby incorporated herein by this reference.

TECHNICAL FIELD

This disclosure relates, generally, to the field of catheters and, more particularly, to a catheter assembly and to a catheter handle of the catheter assembly.

BACKGROUND

The applicant has developed a method of manufacturing a medical use electrical lead which has particular application for use as a catheter sheath. This method is described in International Patent Application No. PCT/AU2001/001339, filed Oct. 19, 2001, entitled, "An Electrical Lead," and International Patent Application No. PCTAU2005/000834, filed Jun. 10, 2005, entitled "A Process of Manufacturing an Electrical Lead."

The methods described in the above patent applications result in an exceedingly good catheter sheath that provides good signal transmission characteristics, a device with minimal, if any, raised formations (which could snare on a patient's tissue), is very flexible but has good torque characteristics and is easy to use by a clinician. However, the manufacturing process involves a number of steps and can be labour-intensive, resulting in increased manufacturing costs.

Also, where the catheter sheath enters the handle, conductors of the sheath need to be exposed to access the conductors for connection to a connector to be attached to electrical equipment, such as diagnostic or therapeutic equipment, with which the catheter sheath is used. This results in further manufacturing steps.

DISCLOSURE

In a first aspect, there is provided a catheter assembly which includes:
 a catheter handle having a handle body defining a bore and having a proximal part and a distal end;
 a catheter sheath having a proximal part received in the bore of the handle body, the catheter sheath projecting from the distal end of the catheter handle and the proximal part of the catheter sheath carrying a series of spaced electrically conductive members, each conductive member being electrically connected to a conductor extending in the catheter sheath from the proximal part towards a distal end of the catheter sheath; and
 a carrier arranged in the bore of the handle body, the carrier carrying a series of spaced electrical contacts with each contact being configured to make electrical contact with one of the electrically conductive members of the catheter sheath.

The carrier may include a substantially rigid strip, such as a printed circuit board, carrying the series of spaced contacts. The carrier may include a displaceable element axially displaceably arranged in the bore of the handle body, the displaceable element defining a receiving formation for receiving the proximal part of the catheter sheath.

The strip may be fixed to the displaceable element so that the catheter sheath and the strip move in unison.

The catheter sheath may comprise an elongate member having an inner member, a plurality of conductors arranged on the inner member to extend along the inner member and an outer layer of a non-conductive material overlying the conductors. Preferably, the conductors are helically wound about the inner member of the elongate member.

In respect of each conductive member, an opening may be formed through the outer layer of the elongate member from an outer surface to at least one of the conductors with a conductive material contained in the opening forming the conductive member.

In an embodiment, the assembly may include an annular conductive element associated with each conductive member, the conductive element being in electrical contact with its associated conductive member. Each conductive element may be swaged in position about the elongate member over its associated opening to be in conductive communication with the at least one conductor via the conductive member in the opening.

In another embodiment, each conductive element may be formed integrally with its associated electrical contact, each conductive element being in a close fit about an outer surface of the catheter sheath to abut against, and make electrical contact with, the conductive member in its associated opening in the catheter sheath. By "close fit" is meant that the conductive element grips the outer surface of the catheter sheath with sufficient force to ensure electrical contact is made between the conductive element and the conductive material contained in the opening of the catheter sheath.

Further, each conductive element may be dimensioned to extend from an outer surface of the catheter sheath.

In a second aspect, there is provided a catheter handle which includes:
 a handle body defining a bore; and
 a carrier contained in the bore, the carrier having a series of spaced electrical contacts with the contacts being configured to make electrical contact with a series of axially spaced, annular conductive members arranged on a proximal part of a catheter sheath, the proximal part of the catheter sheath being receivable in the carrier to be held in a fixed axial position relative to the carrier.

The carrier may comprise a displaceable element arranged in the bore of the handle body to be axially displaceable in the bore. Further, the carrier may include a substantially rigid strip carrying the series of spaced contacts. The strip may be fixed to the displaceable element to move in unison with the displaceable element.

Each contact may include a resiliently flexible element extending from the strip. In an embodiment, each contact may substantially circumscribe the catheter sheath to make electrical contact with an associated conductive member of the catheter sheath.

BRIEF DESCRIPTION OF THE DRAWINGS

FIG. 1 shows a three-dimensional view of an embodiment of a catheter assembly including an embodiment of a catheter handle with a catheter sheath projecting from the catheter handle;

FIG. 2 shows a cross-sectional side view of the catheter assembly of FIG. 1;

FIG. 3 shows a three-dimensional, exploded view of a part of the catheter assembly of FIG. 1;

FIG. 4 shows a three-dimensional view of the part of the catheter assembly of FIG. 3;

DETAILED DESCRIPTION

Figure 5:
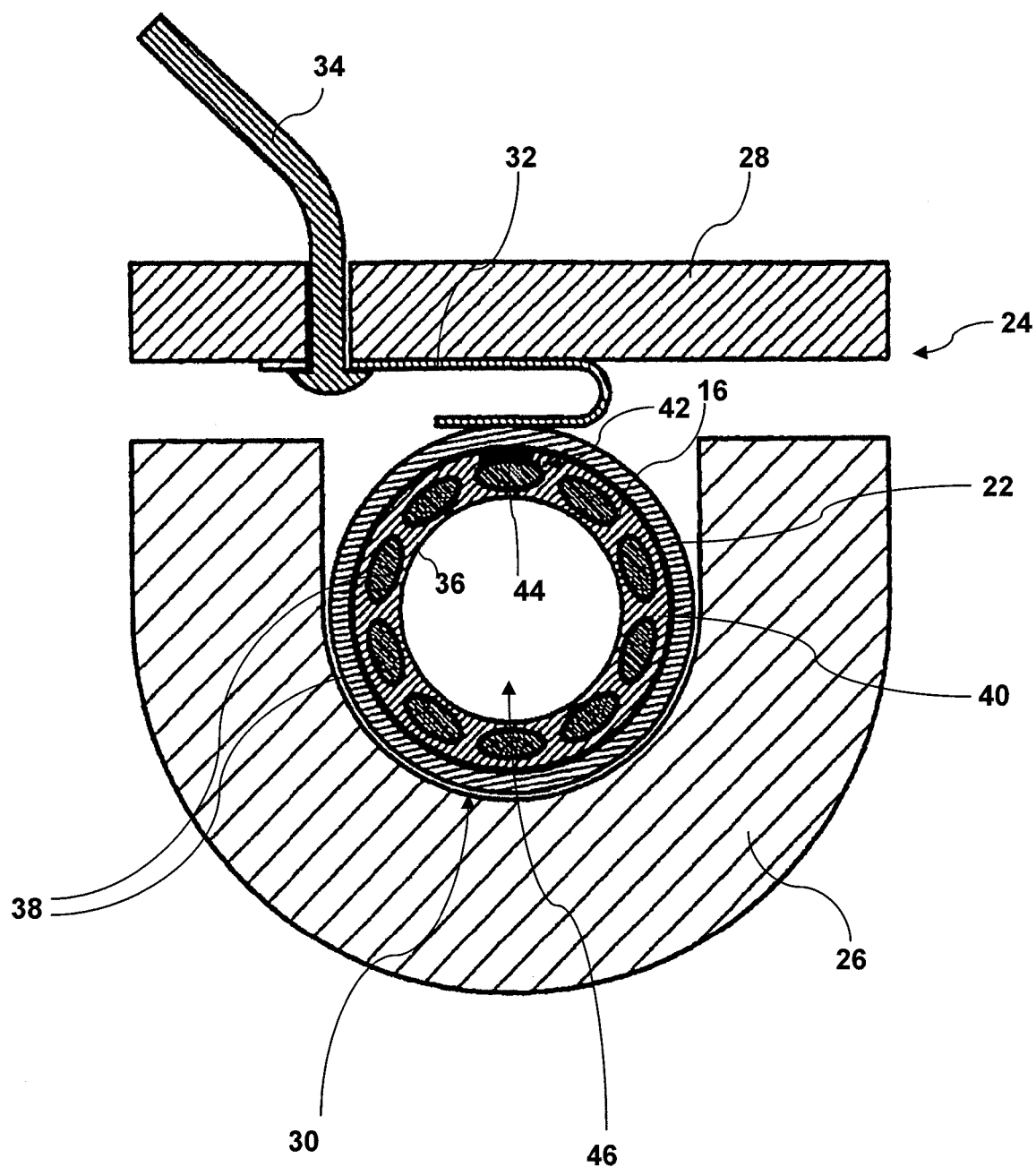
FIG. 5 shows, on an enlarged scale, a cross-sectional transverse view of the part of the catheter assembly of FIG. 4.

In the drawings, reference numeral 10 generally designates an embodiment of a catheter assembly. The catheter assembly 10 comprises a catheter handle 12 having a handle body 14. A catheter sheath 16 projects from a distal end of the handle body 14 with a proximal part 18 (FIG. 2) of the catheter sheath 16 being received in a bore 20 defined by the handle body 14.

As shown in greater detail in FIG. 3 of the drawings, the proximal part 18 of the catheter sheath 16 carries a plurality of axially spaced, annular electrically conductive elements or rings 22. As will be described in greater detail below, each ring, 22 is in electrical contact with a conductor of the catheter sheath 16.

A carrier 24 is arranged in the bore 20 of the handle body 14. The carrier 24 comprises two parts, a rod-like displaceable element 26 and a substantially rigid strip in the form of a printed circuit board (PCB) 28. The displaceable element 26 defines an axially extending channel 30 within which that part of the proximal part 18 of the catheter sheath 16 which carries the rings 22 is received. The PCB 28 is received over that part of the proximal part 18 of the catheter sheath 16 received in the channel 30 of the displaceable element 26.

The PCB 28 carries a plurality of axially spaced contacts 32, one of which is shown in greater detail in FIG. 5 of the drawings. A contact 32 is associated with each ring 22 of the catheter sheath 16. Each contact 32 is electrically connected to an electrical connector 34 projecting through the PCB 28. Conductors (not shown) extend from the connectors 34 to a connecting plug (also not shown) associated with the catheter handle 12 for connecting the catheter assembly 10 to electrical equipment such as diagnostic equipment or therapeutic equipment.

As illustrated schematically in FIG. 5 of the drawings, the catheter sheath 16 comprises an inner member 36. A plurality of conductors 38 are helically wound about the inner member 36 to extend from the proximal part 18 of the catheter sheath 16 to a distal end of the catheter sheath 16 on which electrodes are arranged. The distal end of the catheter sheath is not shown in the drawings for the sake of clarity.

The conductors 38 are, in turn, covered by an outer layer or covering 40 of a visually transparent material. The catheter sheath 16 is manufactured in accordance with the manufacturing methods described in the International Patent Applications referenced above.

To access the relevant conductor 38, an opening 42 is formed through the outer layer 40 of the catheter sheath 16. The opening 42 is formed by an appropriate cutting technique that can cut the opening to the required accuracy, such as, for example, a laser cutting technique. The opening 42, so formed, is filled with a conductive material to form a conductive member 44. A ring 22 is applied to the catheter sheath 16 and is positioned over the opening 42. The ring 22 is swaged in position on the catheter sheath 16 so that the ring 22 makes electrical contact with the conductive member 44 and, via the conductive member 44, with its associated electrical conductor 38. It will be appreciated that each ring 22 is fitted in a similar manner to the proximal part 18 of the catheter sheath 16.

Each ring 22 is dimensioned so that it stands proud of the outer surface of the outer layer 40 of the catheter sheath 16 to make contact with its associated contact 32 in a slip ring-fashion. It will, however, also be appreciated that each ring 22 could be substantially flush with the outer layer 40 of the catheter sheath 16 with its associated contact 32 still being able to make electrical contact with the ring 22.

It is to be noted that, as a result of the method of manufacturing the catheter sheath 16, a catheter sheath 16 is provided which has an unimpeded lumen 46. The carrier 24 is mounted in a sleeve 48 (FIG. 2) of a steering control mechanism 50 of the catheter assembly 10. The arrangement is such that the carrier 24 is fast with the sleeve 48. The sleeve 48 is, further, integrally formed with a steering control knob 52 arranged at a distal end of the handle body 14 of the catheter handle 12. The catheter assembly 10 includes a steerable stylet (not shown) received in the lumen 46 of the catheter sheath 16. The stylet comprises two parts, a tubular member and an actuator or wire received in the passage of the tubular member. A distal end of the tubular member has a bend-enhancing portion and the distal end of the actuator is fast with the distal end of the tubular member of the stylet. For example, the stylet is manufactured in accordance with the teachings of International Patent Application No. PCT/AU2005/000216, filed Feb. 18, 2005 and entitled "A Steerable Catheter."

The tubular member of the stylet is, in turn, made fast with the sleeve 48 of the steering control mechanism 50 of the catheter assembly 10. The actuator is made fast with a proximal part of the handle body 14 of the catheter handle 12 so that relative displacement between the steering control mechanism 50 and the handle body 14 causes bending of the stylet at the bend-enhancing region and, in so doing, results in steerability of the distal end of the catheter sheath 16.

The catheter handle 12 also includes a projection control mechanism 54. The projection control mechanism 54 has a projection control knob 56 with a sleeve 58 extending proximally from the projection control knob 56. The sleeve 58 lies within the steering control mechanism 50 and the carrier 24 is fast with the sleeve 58 of the projection control mechanism 54. The projection control mechanism 54 is used to project the distal end of the catheter sheath 16 beyond the distal end of the stylet received in the lumen 46 of the catheter sheath 16 so that the distal end of the catheter sheath 16 can be inserted into hard to reach places at a site in a patient's body. It is noted that the PCB 28 moves with the projection control mechanism 54 so that the contacts 32 of the PCB 28 are always in contact with their associated rings 22.

As described above, the distal end of the catheter sheath 16 carries electrodes. In a preferred embodiment, the electrodes are formed by swaging rings on to the distal end of the catheter sheath 16 in a similar manner to that described above with reference to the rings 22 at the proximal part 18 of the catheter sheath 16. The only difference is that, at the distal end, rings forming the electrodes are swaged onto the catheter sheath 16 so that outer surfaces of the electrodes are substantially flush with the outer surface of the catheter sheath 16. This reduces the likelihood of the electrodes snagging on tissue in a patient's body.

Figure 6:
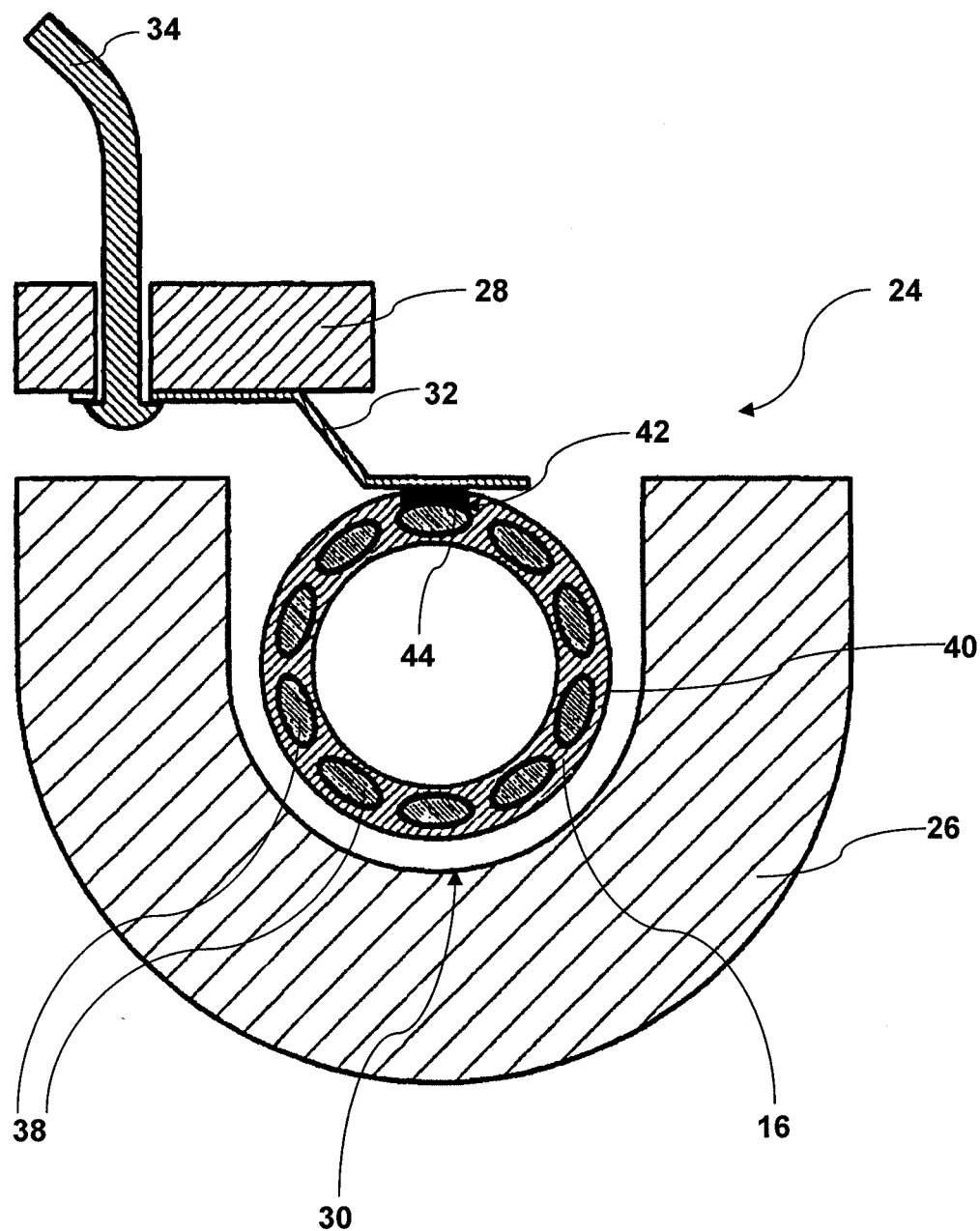
FIG. 6 shows, on an enlarged scale, a cross-sectional transverse view of another embodiment of a catheter assembly.

In FIG. 6 of the drawings, a further embodiment of the catheter assembly 10 is illustrated. With reference to the previous drawings, like reference numerals refer to like parts unless otherwise specified.

In this embodiment, the rings 22 are omitted. Each contact 32 is shaped to make direct electrical contact with its associated conductive member 44. Hence, by omitting the rings 22, manufacturing steps are reduced, which, in turn, results in lower production costs of the catheter assembly 10.

Figure 7:
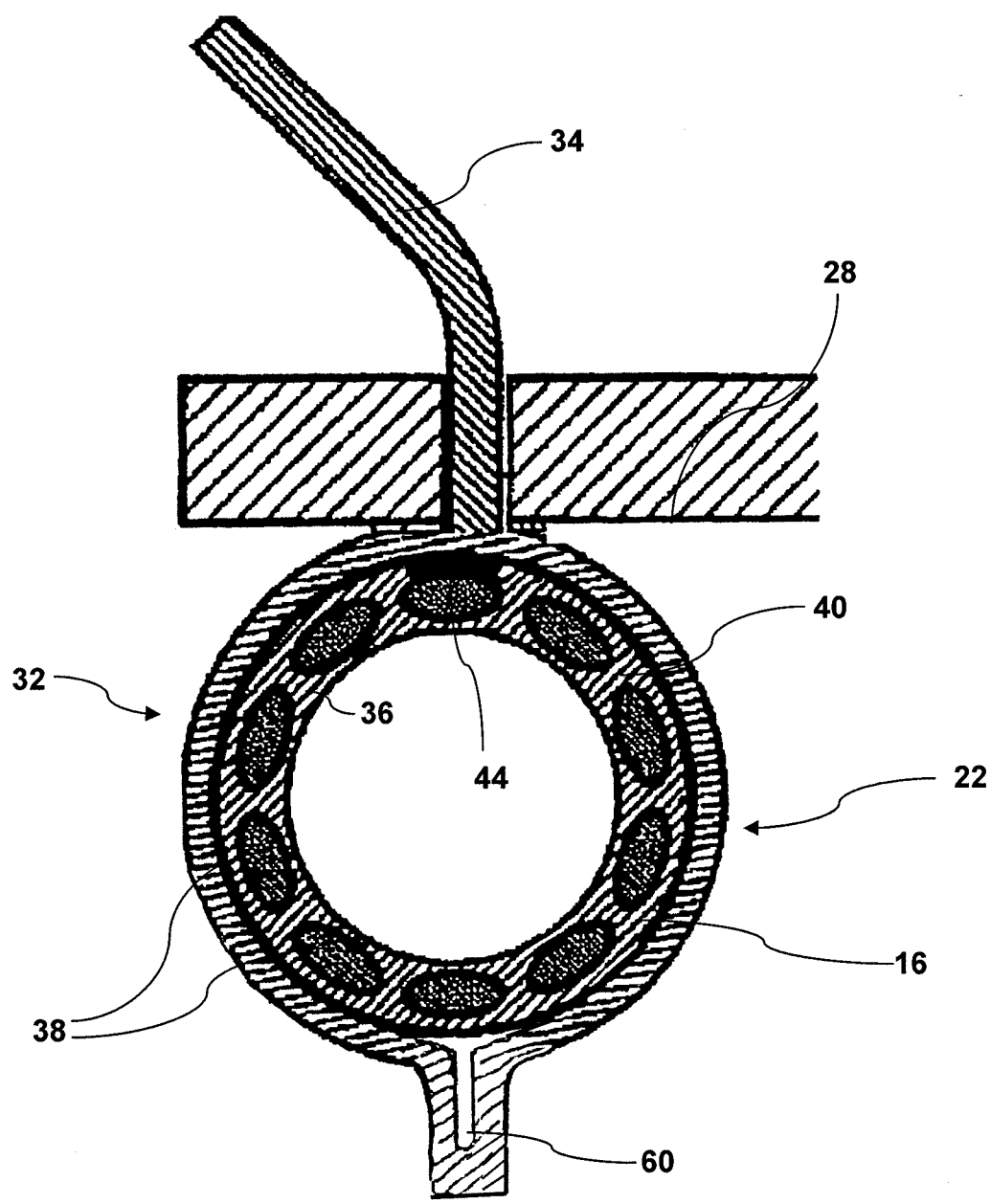
FIG. 7 shows, on an enlarged scale, a cross-sectional transverse view of a further embodiment of a catheter assembly.

Another embodiment of a catheter assembly 10 is illustrated in FIG. 7 of the drawings. Again, with reference to the previous drawings, like reference numerals refer to like parts unless otherwise specified.

In this embodiment, each contact 32 is, itself, formed as the ring 22. The annular contact 32 is placed about the outer surface of the outer layer 40 of the catheter sheath 16. In this embodiment, the annular contact 32 is oversized and is crimped in position, as shown at 60, so that the ring 22, so formed, is a close fit about the catheter sheath 16 to make electrical contact with the conductive member 44 in the opening 42 associated with that ring 22.

In a variation of this embodiment, the ring 22 may comprise two arcuate limbs which, when placed about the catheter sheath 16, substantially circumscribe the outer surface of the catheter sheath 16. Free ends of the limbs may or may not touch, but the limbs of the ring 22 are sufficiently resiliently flexible to ensure that they are in a close fit about the catheter sheath 16 to make electrical contact with the conductive member 44 in the opening 42 associated with that ring 22.

In the embodiments described with reference to FIG. 7, there are fewer manufacturing steps, which results in reduced production costs.

Hence, it is an advantage of the disclosed embodiments that a system is provided for connecting a catheter sheath electrically to equipment, such as therapeutic equipment or diagnostic equipment, in a more cost-effective manner. A PCB of the type illustrated is far cheaper to manufacture than connecting plugs with associated conductors, etc. Also, the handle body 12 is simplified in comparison with other catheter handle bodies of which the applicants are aware. This further reduces the cost of the catheter assembly 10.

In addition, by swaging the rings 22 onto the catheter sheath 16, the number of manufacturing steps for establishing electrical connection between conductors of the catheter sheath and the conductive part of the catheter handle is greatly reduced and manufacturing is simplified.

It will be appreciated by persons skilled in the art that numerous variations and/or modifications may be made to the described embodiments without departing from the scope thereof as broadly described. The present embodiments are, therefore, to be considered in all respects as illustrative and not restrictive.

The invention claimed is:

1. A catheter assembly, comprising:
   a catheter handle having a handle body defining a bore and having a first proximal part and a distal end;
   a catheter sheath having a second proximal part received in the bore of the handle body, the catheter sheath projecting from the distal end of the catheter handle and the second proximal part of the catheter sheath carrying a series of spaced electrically conductive members, each conductive member being electrically connected to a conductor extending in the catheter sheath from the second proximal part towards a distal end of the catheter sheath; and
   a carrier axially displaceably arranged in the bore of the handle body during use, the carrier carrying a series of spaced electrical contacts with each contact being configured to make electrical contact with one of the electrically conductive members of the catheter sheath.

2. The assembly of claim 1, wherein the carrier includes a substantially rigid strip carrying the series of spaced contacts.

3. The assembly of claim 2, wherein the carrier includes a displaceable element axially displaceable in the bore of the handle body, the displaceable element defining a receiving formation for receiving the second proximal part of the catheter sheath.

4. The assembly of claim 3, wherein the strip is fixed to the displaceable element so that the catheter sheath and the strip move in unison.

5. The assembly of claim 1, wherein the catheter sheath comprises an elongate member having an inner member, a plurality of conductors arranged on the inner member to extend along the inner member and an outer layer of a non-conductive material overlying the conductors.

6. The assembly of claim 5, wherein the conductors are helically wound about the inner member of the elongate member.

7. The assembly of claim 5, wherein in respect of each conductive member, an opening is formed through the outer layer of the elongate member from an outer surface to at least one of the conductors with a conductive material contained in the opening forming the conductive member.

8. The assembly of claim 7, further comprising an annular conductive element associated with each conductive member, the conductive element being in electrical contact with its associated conductive member.

9. The assembly of claim 8, wherein each conductive element is swaged in position about the elongate member over its associated opening to be in conductive communication with the at least one conductor via the conductive member in the opening.

10. The assembly of claim 8, wherein each conductive element is formed integrally with its associated electrical contact, each conductive element being in a close fit about an outer surface of the catheter sheath to abut against, and make electrical contact with, the conductive member in its associated opening in the catheter sheath.

11. The assembly of claim 8, wherein each conductive element is dimensioned to extend from an outer surface of the catheter sheath.

12. A catheter handle, comprising:
   a handle body defining a bore; and
   a carrier axially displaceably contained in the bore during use, the carrier having a series of spaced electrical contacts with the contacts being configured to make electrical contact with a series of axially spaced, annular conductive members arranged on a proximal part of a catheter sheath, the proximal part of the catheter sheath being receivable in the carrier to be held in a fixed axial position relative to the carrier.

13. The handle of claim 12, wherein the carrier comprises a displaceable element arranged in the bore of the handle body to be axially displaceable in the bore.

14. The handle of claim 13, wherein the carrier includes a substantially rigid strip carrying the series of spaced contacts.

15. The handle of claim 14, wherein the strip is fixed to the displaceable element to move in unison with the displaceable element.

16. The handle of claim 14, wherein each contact includes a resiliently flexible element extending from the strip.

17. The handle of claim 16, wherein each contact substantially circumscribes the catheter sheath to make electrical contact with an associated conductive member of the catheter sheath.

* * * * *